[54] ETHYLENE CARBONATE PROCESS

[75] Inventors: Dale A. Raines, Wheatridge, Colo.; Oliver C. Ainsworth, Baton Rouge, La.

[73] Assignee: The Dow Chemical Company, Midland, Mich.

[21] Appl. No.: 87,841

[22] Filed: Oct. 24, 1979

[51] Int. Cl.$^3$ ............................................. C07D 317/38
[52] U.S. Cl. ............................ 260/340.2; 260/348.37
[58] Field of Search ........................................ 260/340.2

[56] References Cited

U.S. PATENT DOCUMENTS

| | | | |
|---|---|---|---|
| 2,511,942 | 6/1950 | Prichard | 260/340.2 |
| 2,773,070 | 12/1956 | Lichtenwalter et al. | 260/340.2 |
| 2,924,608 | 2/1960 | Mills | 260/340.2 |
| 2,993,908 | 7/1961 | Millikan et al. | 260/340.2 |
| 2,994,704 | 8/1961 | Crosby et al. | 260/340.2 |
| 3,214,892 | 11/1965 | Holbrook | 55/68 |
| 3,535,341 | 10/1970 | Emmons et al. | 260/340.2 |
| 3,535,341 | 10/1970 | Emmons et al. | 260/340.2 |
| 3,535,342 | 10/1970 | Emmons | 260/340.2 |
| 3,629,343 | 12/1971 | Levin | 260/635 E |
| 3,748,345 | 7/1973 | De Pasquale | 260/340.2 |

OTHER PUBLICATIONS

W. J. Peppel, Industrial and Engineering Chemistry, vol. 50, No. 5, May 1958, pp. 767–770.

*Primary Examiner*—Norma S. Milestone
*Attorney, Agent, or Firm*—A. C. Ancona

[57] ABSTRACT

An improved process for making ethylene carbonate wherein ethylene oxide and carbon dioxide are passed over an anion exchange resin catalyst and wherein the ethylene oxide and carbon dioxide reactants are absorbed from the effluent of an ethylene oxide reactor, desorbed and used as feed to the ethylene carbonate plant without further purification.

7 Claims, 1 Drawing Figure

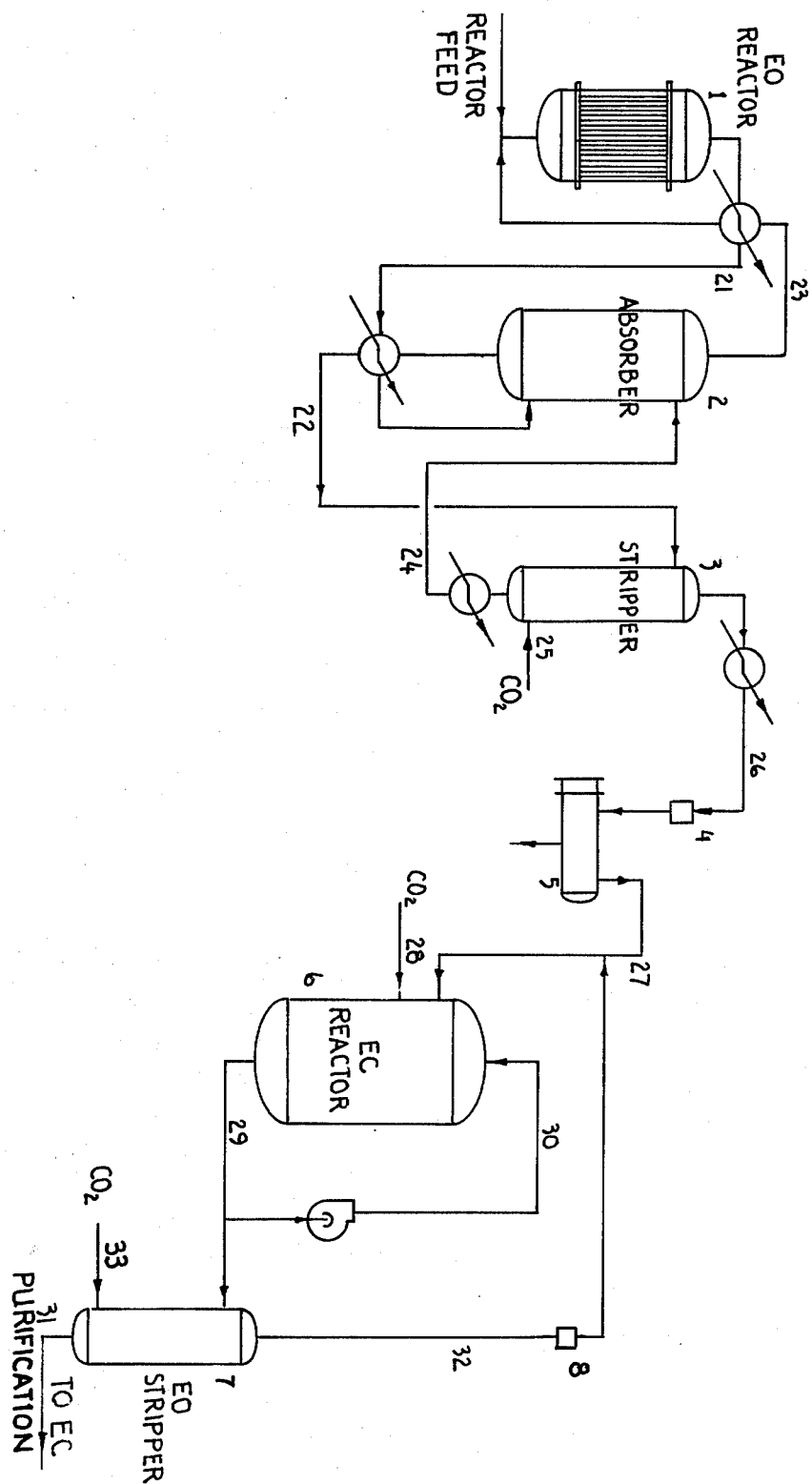

ETHYLENE CARBONATE PROCESS

BACKGROUND OF THE INVENTION

The preparation of alkylene carbonates by reacting an alkylene oxide and carbon dioxide is well known. The general conditions for the reaction are the use of temperatures in the approximate range of 100°–250° C. Superatmospheric pressures of about 10–300 atmospheres are employed. A reaction temperature of about 160°–200° C. and a pressure of 50–150 atmospheres are usually preferred. The reactants are used in about equal molar proportions with the carbon dioxide normally in slight excess.

Known catalysts for the reaction include inorganic bases such as sodium hydroxide and sodium carbonate and organic nitrogen bases such as tertiary amines, quaternary ammonium bases, and salts of these nitrogen bases such as their carbonates and halides. For example, aliphatic tertiary amines such as trimethylamine, aromatic tertiary amines such as pyridine and quinoline, quaternary ammonium hydroxides such as tetraethyl ammonium hydroxide, trimethyl benzyl ammonium hydroxide, dialkyl piperidinium hydroxide, and the carbonates, bicarbonates, and halides of such hydroxides are all known to catalyze the reaction. Catalyst concentrations of 0.1–5 percent based on the weight of alkylene oxide are conventional.

Other catalysts disclosed in the patent literature are anion exchange resins containing quaternary ammonium chloride groups (U.S. Pat. No. 2,773,070), hydrazine or the hydrohalide salt thereof (U.S. Pat. No. 3,535,341) and quanidine and its salts (U.S. Pat. No. 3,535,342). Catalysts known to the art generally are effective for the purpose and they provide fairly high conversions of the reactants and generally good yields of the desired cyclic carbonates. These yields usually are about 70–90 percent of the theoretical. The latter two patents claim conversions and yields each in excess of 95%.

The manufacture of alkylene carbonates is effectively accomplished in conjunction with an alkylene oxide plant. Thus, for example, ethylene carbonate production is advantageously located in the proximity of an ethylene oxide plant.

The ethylene oxide obtained from the direct oxidation of ethylene is usually not pure enough to be employed as a feed to an ethylene carbonate plant without prior purification. It has now been discovered that when ethylene oxide is recovered from the effluent of such a plant by absorbing it in ethylene carbonate, the ethylene oxide together with the carbon dioxide absorbed can be employed without further purification as feed to a process for making ethylene carbonate. Thus, a simple stripping and drying of these gases from the ethylene carbonate absorbent provides reactants of acceptable purity for this process.

SUMMARY OF THE INVENTION

In the manufacture of ethylene carbonate (EC) from ethylene oxide (EO) and carbon dioxide ($CO_2$), wherein the EO and $CO_2$ are obtained as the purified products of the reaction of ethylene and oxygen over a silver catalyst, i.e., via direct oxidation ethylene oxide (DOEO), an improved integrated process is obtained by absorbing the DOEO reactor effluent in ethylene carbonate, desorbing (stripping) the $CO_2$ and EO from the EC absorbent and, thereafter, without further purification except for a drying step, employing these gases as feed to an EC manufacturing process. All that is necessary is to add sufficient $CO_2$ from another source to provide a molar excess over the stoichiometric requirements.

DETAILED DESCRIPTION OF THE INVENTION

The effluent of an ethylene oxide DOEO reactor is contacted with ethylene carbonate, whereby ethylene oxide, water, and carbon dioxide are absorbed. The absorbed gases are desorbed by employing heat and stripping with an inert gas (preferably $CO_2$), drying and feeding the desorbed $CO_2$ and EO, together with sufficient additional $CO_2$ to provide an excess over the stoichiometric amount, to a reactor containing a catalyst for the reaction of EO and $CO_2$ to produce ethylene carbonate. A preferred catalyst is a strong anion exchange resin containing trimethylbenzyl ammonium chloride groups. Other strong anion exchange resins containing quaternary ammonium groups are also useful. Such exchange resins are produced under the names DOWEX XF-4155L, DOWEX MSA-1, and DOWEX 21K, and are available from The Dow Chemical Company. Those resins designated Amberlite IRA-900 series and Amberlite IRA 400 series are anion exchange resins which are available from Rohm and Haas; and Duolite A-101D, Duolite ES-131 and, Duolite A-161 are anion exchange resins available from Diamond Shamrock and are likewise useful as catalysts for the process. The product ethylene carbonate is separated from any unconverted reactants (which are recycled to the EC reactor) and subsequently distilled to remove any higher boiling impurities, e.g., polycarbonates.

The absorbing and stripping steps which are an integral part of the present process are described in greater detail in the copending application of one of us, filed Aug. 17, 1979, as Ser. No. 067,580 under the title "ETHYLENE OXIDE RECOVERY".

The integrated process in which an ethylene oxide reactor is coupled to an ethylene carbonate process via absorbing and stripping steps is described with reference to the drawing as follows:

The effluent of the EO reactor 1 is passed via conduit 21 to an absorption (absorber) column 2 containing ethylene carbonate (maintained at a temperature of 35°–50° C.) wherein EO and $CO_2$ are absorbed; the ethylene which is not absorbed is returned via conduit 23 to the EO reactor. The EC absorbent containing dissolved EO and $CO_2$ is then sent via conduit 22 to a desorption (stripper) column 3 where it is heated (maintained at a temperature of 90°–150° C.) and contacted with an inert stripping gas ($CO_2$ or $N_2$) introduced via line 25 at a temperature of about 110° C. The stripped gases (EO and $CO_2$) are removed through conduit 26 and the EC absorbent is recycled via conduit 24 to absorber 2. The stripped gases are compressed to a pressure of (100–500 psia) by compressor 4 and sent through condenser 5 (maintained at a temperature of 0°–25° C.) to condense out water prior to being fed via conduit 27 to the EC reactor 6 which contains an anion exchange resin catalyst. The pressure in reactor 6 is maintained at about 100–500 psia, but somewhat lower than that of the incoming feed gases. Additional $CO_2$ is fed to the reactor (if needed to provide an adequate molar excess) via line 28. The ethylene carbonate is removed via conduit 29, excess $CO_2$ is recycled to the EC reactor via conduit 30 and any dissolved unreacted EO is removed from the EC in EO stripper 7 to which $CO_2$ is fed via conduit 33 as a stripping gas which is also used as a source of make-up $CO_2$ to the reactor 6 and is returned thereto via conduit 32 and passed through compressor 8 where the gases are raised to a pressure sufficient to overcome the pressure in reactor 6 to which they are fed as reactants, while the product EC is sent to a purification step via conduit 31.

The following examples illustrate the invention:

EXAMPLE 1

A synthetic gas mixture, representative of a stream stripped from an EC absorber of the effluent of an EO plant wherein air is used as the oxygen source, which contained about 1 mole % EO, 9 mole % $CO_2$ and 2 mole % water vapor, was compressed and then sent through a condenser to remove the water. Thereafter the gas stream was passed over a catalyst in a reaction vessel which consisted of a packed bed of an anion exchange resin (DOWEX XF-4155L) containing trimethylbenzyl ammonium chloride groups. Additional $CO_2$ was added to the reactor to produce a reaction mixture containing 8.3 mole % EO, 91.7 mole % $CO_2$, 260 ppm (wt.) acetaldehyde. The resin bed had a volume of 95 ml. and the process parameters were:

flow rate = 0.5 scf/hr.
temp. = 105°–106° C.
pres. = 350 psig.

At substantially 100% selectivity the yield was 87% ethylene carbonate.

EXAMPLES 2–6

In the same equipment and in the manner of Example 1, but employing different ratios of reactants, reaction parameters and catalysts. Other experiments were conducted which are shown in the following table. Mole percent of EO alone is given, the balance consisting of $CO_2$.

| Ex. | EO Mole % | Acetald. (ppm) | Exch.* Resin | Press. (psig) | Temp. (°C.) | Flow SCF/hr. | %Yield EC |
|---|---|---|---|---|---|---|---|
| 2 | 14.0 | 260 | XF4155L | 220 | 95 | 1.52 | 45 |
| 3 | 13.0 | 130 | " | 220 | 100 | 1.00 | 69 |
| 4 | 1.8 | — | MSA-1 | 220 | 105 | 3.60 | 79 |
| 5 | 1.8 | — | DC-Z-6020 | 220 | 115 | 1.77 | 89 |
| 6 | 1.6 | — | 21K | 220 | 115 | 1.77 | 92 |

*XF4155L, MSA-1, and 21-K are anion exchange resins containing trimethylbenzyl ammonium groups, all of which are products of The Dow Chemical Company.
DC-Z-6020 is a Dow-Corning silane fluid which contains N-(2-aminoethyl)-3-aminopropyl trimethoxysilane. This was coated on alumina pellets and treated with bromopropane to quaternize the amine groups.

We claim:

1. An integrated process for making ethylene carbonate by (1) reacting ethylene with oxygen over a silver catalyst to produce ethylene oxide, (2) contacting the product gases from said reaction with ethylene carbonate to absorb ethylene oxide and carbon dioxide, (3) stripping said ethylene oxide and carbon dioxide from the said ethylene carbonate absorbent by contacting with an inert gas, (4) reacting said ethylene oxide and carbon dioxide over an anion exchange resin to form ethylene carbonate and (5) recovering said ethylene carbonate.

2. Process of claim 1 wherein additional carbon dioxide is supplied to the reactor to provide a stoichiometric excess of carbon dioxide with respect to ethylene oxide therein.

3. Process of claim 2 wherein unreacted carbon dioxide is recovered and recycled to the ethylene carbonate reactor.

4. Process of claim 1 wherein stripping step (3) is accomplished by heating and employing carbon dioxide as the inert gas.

5. The process of claim 1 wherein the ethylene oxide and carbon dioxide stripped from the absorbent are dried prior to passing into the ethylene carbonate reactor.

6. The process of claim 1 wherein the anion exchange resin contains trimethylbenzyl ammonium halide groups.

7. In a process for making ethylene carbonate by reacting ethylene oxide and carbon dioxide in the presence of a quaternary ammonium halide the improvement which comprises
   (1) employing ethylene carbonate as absorbent for the ethylene oxide and carbon dioxide in the effluent product gas from the partial oxidation of ethylene,
   (2) stripping ethylene oxide and carbon dioxide from said ethylene carbonate by heating and contacting with an inert gas,
   (3) adding sufficient carbon dioxide to the gas mixture of step (2) to provide a molar excess thereof with respect to the ethylene oxide present,
   (4) reacting said ethylene oxide and carbon dioxide in the presence of an anion exchange resin which contains quaternary ammonium groups to form ethylene carbonate,
   (5) separating said ethylene carbonate from unconverted reactants,
   (6) recycling said unconverted reactants to the ethylene carbonate reaction, and
   (7) recovering said ethylene carbonate.

* * * * *